United States Patent
Kamei et al.

(10) Patent No.: US 9,610,079 B2
(45) Date of Patent: Apr. 4, 2017

(54) MEDICAL STAPLE AND MAGAZINE

(75) Inventors: Toshiharu Kamei, Utsunomiya (JP); Kazuaki Kato, Utsunomiya (JP)

(73) Assignee: MANI, INC., Tochigi (JP)

( * ) Notice: Subject to any disclaimer, the term of this patent is extended or adjusted under 35 U.S.C. 154(b) by 721 days.

(21) Appl. No.: 12/744,527

(22) PCT Filed: Nov. 28, 2008

(86) PCT No.: PCT/JP2008/071695
§ 371 (c)(1),
(2), (4) Date: Aug. 4, 2010

(87) PCT Pub. No.: WO2009/069767
PCT Pub. Date: Jun. 4, 2009

(65) Prior Publication Data
US 2011/0029015 A1 Feb. 3, 2011

(30) Foreign Application Priority Data
Nov. 29, 2007 (JP) .................. 2007-308253

(51) Int. Cl.
*A61B 17/068* (2006.01)
*A61B 17/064* (2006.01)

(52) U.S. Cl.
CPC ...... *A61B 17/0684* (2013.01); *A61B 17/0644* (2013.01)

(58) Field of Classification Search
CPC . A61B 17/064; A61B 17/0644; A61B 17/068; A61B 17/0682; A61B 17/0684; A61B 17/0686; A61B 17/072; A61B 17/07207; A61B 17/083; A61B 17/08; A61B 2017/0645; A61B 2017/0646

USPC ......... 606/139, 142, 143, 213, 219, 220, 75; 227/175.1, 176.1, 181.1
See application file for complete search history.

(56) References Cited

U.S. PATENT DOCUMENTS

| | | | | |
|---|---|---|---|---|
| 816,026 A | * | 3/1906 | Meier | 606/221 |
| 2,684,070 A | * | 7/1954 | Kelsey | 606/221 |
| 2,817,339 A | * | 12/1957 | Sullivan | 606/221 |

(Continued)

FOREIGN PATENT DOCUMENTS

| | | |
|---|---|---|
| JP | 60-68841 A | 4/1985 |
| JP | 5-003302 B1 | 1/1993 |
| JP | 2000-217829 A | 8/2000 |

*Primary Examiner* — Dianne Dornbusch
(74) *Attorney, Agent, or Firm* — Shlesinger, Arkwright & Garvey LLP

(57) ABSTRACT

There are provided a medical staple realizing smooth feeding when loaded in a magazine and a magazine which can realize stable feeding by using the medical staple. Where the medical staple includes a body portion; and a pair of legs formed at both ends of the body portion, wherein the legs are tilted at an angle in which the legs become closer to each other and either one leg is twisted with respect to a plane including the body portion and the other leg in the out-of-plane direction. The magazine includes a body guiding portion which has a size substantially equal to or slightly smaller than the length of the body portions of the staples and carries and guides the body portions thereon; wherein the plurality of staples are loaded in a state where the legs are tilted to the downstream side in the discharge direction and the body portions to the upstream side in the discharge direction.

5 Claims, 2 Drawing Sheets

(56) References Cited

U.S. PATENT DOCUMENTS

| | | | |
|---|---|---|---|
| 4,582,237 A | | 4/1986 | Storace |
| 4,669,647 A | | 6/1987 | Storace |
| 5,007,921 A | * | 4/1991 | Brown .......................... 606/221 |
| 5,181,645 A | * | 1/1993 | Matsutani et al. ......... 227/177.1 |
| 5,258,009 A | * | 11/1993 | Conners ....................... 606/219 |
| 5,413,584 A | * | 5/1995 | Schulze ........................ 606/219 |
| 5,456,400 A | * | 10/1995 | Shichman et al. ......... 227/176.1 |
| 5,497,933 A | * | 3/1996 | DeFonzo et al. ........... 227/175.1 |
| 5,715,987 A | * | 2/1998 | Kelley et al. .............. 227/175.1 |
| 5,788,698 A | * | 8/1998 | Savornin ....................... 606/75 |
| 5,908,149 A | * | 6/1999 | Welch et al. .............. 227/176.1 |
| 7,056,330 B2 | * | 6/2006 | Gayton ......................... 606/219 |
| 7,112,214 B2 | * | 9/2006 | Peterson et al. .............. 606/220 |
| 7,722,610 B2 | * | 5/2010 | Viola et al. ................... 606/250 |
| 7,887,563 B2 | * | 2/2011 | Cummins ..................... 606/219 |
| 8,381,961 B2 | * | 2/2013 | Holsten et al. ............ 227/175.1 |
| 2004/0006372 A1 | * | 1/2004 | Racenet et al. ............... 606/219 |
| 2004/0199182 A1 | | 10/2004 | Milliman et al. |
| 2005/0273138 A1 | * | 12/2005 | To et al. ....................... 606/219 |
| 2006/0191974 A1 | * | 8/2006 | Matsutani et al. ......... 227/175.1 |
| 2008/0161808 A1 | * | 7/2008 | Fox ................................ 606/75 |

\* cited by examiner

ABSTRACT# MEDICAL STAPLE AND MAGAZINE

FIELD OF THE INVENTION

The present invention relates to a medical staple used for suturing biological tissues and a magazine in which a plurality of medical staples is arranged in parallel and loaded in a tilted manner.

DESCRIPTION OF THE RELATED ART

In surgical operations, cut-opened affected parts are sutured by medical staples. Such a medical staple includes a body portion and a pair of legs formed at both ends of the body portion, and has a U-shape when viewed from the front side. The tips of the legs are formed as sharp pointed edges so as to reduce piercing resistance at the time of piercing through biological tissues.

The medical staples are manufactured by bending both ends of a straight steel wire having a circular cross section in the direction in which the ends become closer to each other, when the ends have a predetermined angle before they are perpendicular to the center portion of the wire, relatively moving the cutting edge of a punch in the direction that is orthogonal to the center portion and in which the ends are bent so as to cut the ends, and bending the ends substantially perpendicularly with respect to the center portion (see Patent Document 1).

The thus manufactured medical staples are loaded into a magazine in parallel to be fed to a medical stapler piece by piece. The magazine includes a body supporting portion which supports and guides the center portions (body portions) of the medical staples, hanging portions which hangs from both ends of the body supporting portion, and guiding portions which are formed at the lower ends of the hanging portions and guide the tips of the bent portions (legs) of the medical staples, and is formed in a Ω shape when viewed from the front side (see Patent Document 2). A pusher is provided in the body supporting portion of the magazine and urges the medical staples loaded in the magazine in the anvil direction.

As one example, there is a magazine in which the length of the hanging portions is substantially equal to that of the legs of the medical staples and when the medical staples are placed onto the body supporting portion, the legs become substantially perpendicular to the length direction of the body supporting portion. As another example, there is a magazine in which the length of the hanging portions is shorter than that of the legs of the medical staples and when the medical staples are placed onto the body supporting portion, the tip portions of the legs are tilted in the downstream direction of the urging direction of the pusher and the body portions are tilted in the upstream direction of the urging direction. The magazines are appropriately selectively used according to the functions of the medical staplers.

[Patent Document 1] Japanese Patent Publication No. 5-3302
[Patent Document 2] Japanese Patent Application Laid-Open No. 2000-217829

SUMMARY OF THE INVENTION

It is preferred that the body portion and the pair of legs of the U-shaped medical staple exist in the same plane. However, the material is not necessarily straight in the strict sense but subtle bending and twisting can be caused in the material cut to a predetermined length. In this case, even if precise bending is realized, the tips of the legs are relatively shifted in the out-of-plane direction. The relative shift of the legs caused at this time is due to individual nature of the material (e.g., a residual stress caused in the material or bending and twisting caused at the time of conveyance), and typically varies for each of material production lots. Such relative shift of the legs due to the individual nature of the material is caused freely in the progress of each of the processing steps, and is difficult to be controlled manually.

In addition, even when the material is straight in the strict sense, the tips of the legs are still relatively shifted in the out-of-plane direction if the material is inserted in a slightly tilted manner with respected to the punch at the time of bending. The amount of the relative shift of the legs caused in this case can be easily controlled by adjusting a material feeding device with respect to the punch.

Such medical staples in which the legs are relatively shifted can be smoothly used without causing any particular problems if they are loaded in a magazine in which the size of the hanging portions is substantially equal to the length of the legs and the legs become substantially perpendicular to the length direction of the body supporting portion when the medical staples are placed onto the body supporting portion.

However, if the medical staples are loaded in the magazine in which the length of the hanging portions is shorter than that of the legs of the medical staples and the tip portions of the legs are tilted in the downstream direction of the urging direction of the pusher and the body portions are tilted in the upstream direction of the urging direction when the medical staples are placed onto the body supporting portion, the shifted legs are tangled with the legs of the adjacent medical staple, thereby interfering with smooth movement. As a result, medical staple feeding can be inhibited in surgical operations.

In particular, when a case constituting the medical stapler is formed of a pair of symmetrically-molded plastic molded components integrated while sandwiching the legs at both ends of the medical staple loaded in the magazine, the posture of the magazine can be affected by dimensional tolerance set for the plastic molded components constituting the case (e.g., a step formed between the assembled plastic molded components). As a result, smooth medical staple feeding can be inhibited.

The present invention provides a medical staple realizing smooth feeding when loaded in a magazine and a magazine which can realize stable feeding by using the medical staple.

To address the above problems, the present inventors have tried some experiments, assuming that when the body case of the medical stapler is constituted by a pair of plastic molded components, different dies are used for the pair of plastic molded components so that the pair of plastic molded components cannot be assembled without causing a step and that twisting between the pair of legs cannot be avoided when the medical staple is manufactured.

As a result, the present inventors have confirmed that when the pair of legs constituting the medical staple are in the same plane, smooth feeding can be realized, and have found that the pair of legs between which uncontrollable relative twisting is caused are tangled with the legs of the adjacent medical staple, which inhibits smooth feeding, and that smooth feeding can be realized by relatively twisting the pair of legs to control the twisted state (the angle formed between the pair of legs).

Accordingly, a medical staple according to the present invention includes a body portion; and a pair of legs formed at both ends of the body portion, wherein the legs are tilted at an angle in which the legs become closer to each other and either one of the legs is twisted with respect to a plane including the body portion and the other leg in the out-of-plane direction.

In addition, a magazine according to the present invention in which a plurality of medical staples is arranged in parallel and loaded in state where the legs are tilted includes a body guiding portion which has a size substantially equal to or smaller than a length of the body portions of the medical staples and carries and guides the body portions of the medical staples thereon; hanging portions which hang from both ends of the body guiding portion and have a size smaller than that of the legs of the medical staples; and leg guiding portions which are formed at lower ends of the hanging portions and guide tips of the legs of the medical staples, wherein the plurality of medical staples is loaded in a state where the legs are tilted to a downstream side in the discharge direction and the body portions are tilted to an upstream side in the discharge direction.

In the medical staple (hereinafter, simply called the "staple") according to the present invention, either one of the pair of legs formed at both ends of the body portion is twisted with respect to the plane including the body portion and the other leg in the out-of-plane direction. Thereby, the amount of the shift of the pair of legs can be always a fixed value without being affected by the value of a residual stress varied for each material and the amount of bending or twisting at the time of conveyance. Accordingly, the same amounts of the relative shifts of the pairs of legs of a plurality of staples can be achieved.

In the magazine according to the present invention, the staples are loaded in a state where the body portions of the plurality of staples are placed onto the body guiding portion, the tips of the legs are in contact with the leg guiding portions, and the legs are tilted in the downstream direction of the staple moving direction while the body portions are tilted in the upstream direction. Accordingly, the legs of the adjacent staples loaded in the magazine are substantially parallel and are never tangled. As a result, smooth feeding of the staples can be realized.

EXPLANATION OF THE REFERENCE NUMERALS

Figure 1:
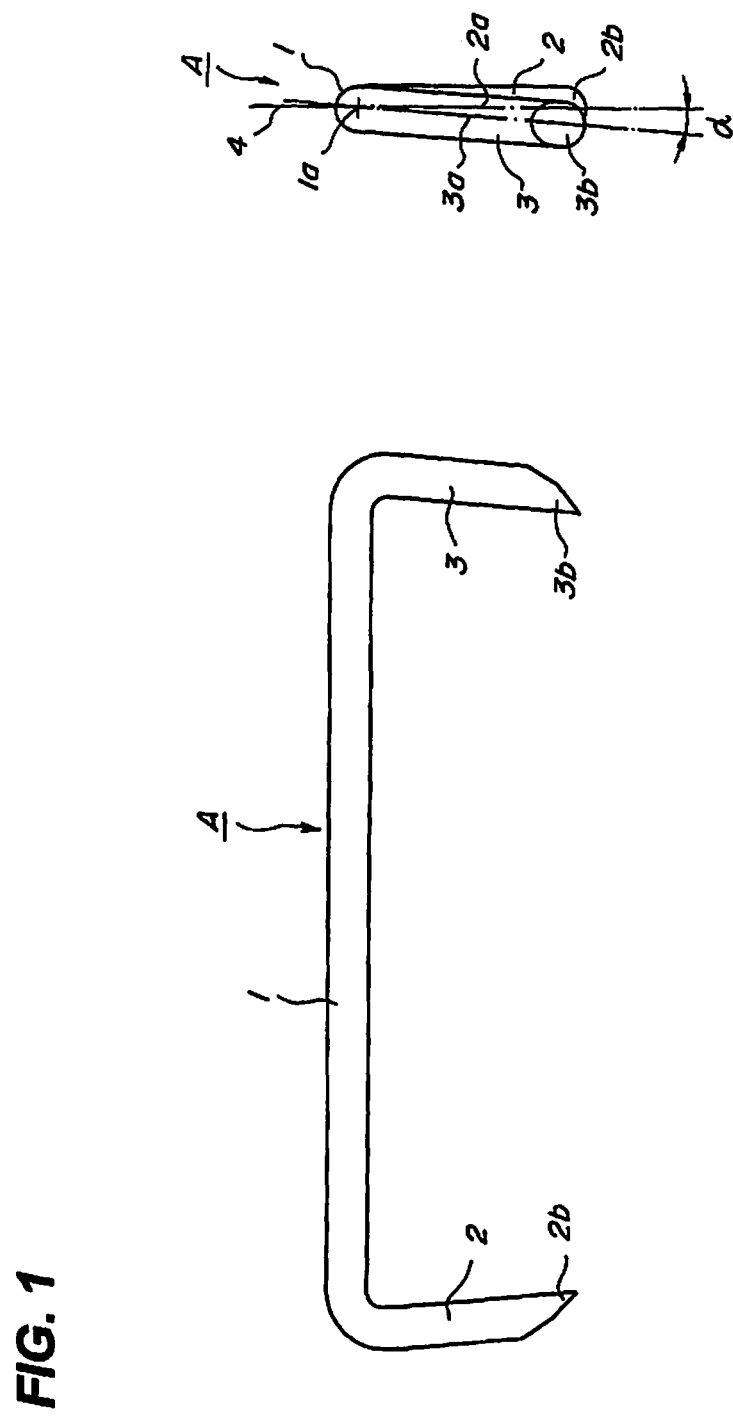
FIG. 1 is a diagram illustrating the configuration of a staple.

A Staple
B Magazine
C Medical stapler
α Twist angle
1 Body portion
1a Centerline
2, 3 Leg
2a, 3a Centerline
2b, 3b Tip
4 Plane
11 Body guiding portion
12 Hanging portion
13 Leg guiding portion
21 Anvil
22 Spring
23 Pusher
25 Ram

DESCRIPTION OF PREFERRED EMBODIMENTS

An exemplary embodiment of a medical staple according to the present invention will be described below with reference to the drawing. FIG. 1 is a diagram illustrating the configuration of the medical staple.

A medical staple A shown in the figure is to suture tissues cut-opened in surgical operations and is formed using a steel wire or a stainless steel wire having a circular cross section. The staple A has a body portion 1 of a predetermined length and a pair of legs 2 and 3 formed by bending the steel wire substantially perpendicularly at both ends of the body portion 1 in a substantially U-shape when viewed from the front side.

The pair of legs 2 and 3 are formed so as to be tilted to the body portion 1 side so that tips 2b and 3b become closer to each other when the staple A is viewed from the front side. Thus, when the body portion 1 is bent by an anvil 21 of a magazine B to make the U-shaped staple A have a substantially square shape as will be described later, the tissues of an affected part can be reliably sutured. The tilt angle of the pair of legs 2 and 3 in the direction in which the legs 2 and 3 become closer to each other is not limited, and may be perpendicular to the body portion 1 or tilted at an angle of about 1° to 3°.

The tips 2b and 3b of the pair of legs 2 and 3 of the staple A are formed as sharp pointed edges so as to reduce resistance at the time of the piercing through the tissues. The shape of the tips 2b and 3b is not limited. In this embodiment, tilted surfaces are formed to the outer side surfaces of the legs 2 and 3 to form sharp edges, thereby constituting the tips 2b and 3b.

In addition, either one of the pair of legs 2 and 3 (e.g., the leg 3; hereinafter, referred to as the "leg 3") formed at both ends of the body portion 1 is twisted with respect to a plane 4 including the body portion 1 and the other leg (e.g., the leg 2; hereinafter, referred to as the "leg 2") in the out-of-plane direction of the plane 4. Specifically, the centerline of the leg 3 is twisted about the center of the body portion 1 with respect to the plane 4 including the centerline of the body portion 1 and the centerline of the leg 2. In other words, a centerline 2a of the leg 2 and a centerline 3a of the leg 3 are twisted each other with reference to a centerline 1a of the body portion 1.

The range of the angle between the centerline 2a of the leg 2 and the centerline 3a of the leg 3 (a twist angle α of the pair of legs 2 and 3) is determined by an experiment. In the experiment, a case manufactured by assembling a pair of symmetrically-molded plastic molded components manufactured by a typical production line is used, the staples with a plurality of twist angles α are manufactured and are loaded in the magazines for the respective angles in advance, each of the magazines is fit into the case, and a handle is operated to compare staple feeding smoothness.

As a result of the above experiment, when the twist angle α between the pair of legs 2 and 3 is in the range of 0° or more and less than 1.9°, substantially smooth feeding can be realized. In addition, when the twist angle α is 0° or more and less than 1.3°, smoother feeding can be realized. Further, when the twist angle α is 0° or more and less than 0.6°, smooth feeding can be realized without any problems at all.

When the twist angle α is in a range larger than 2.5°, the legs of the adjacent staples are tangled so that smooth feeding cannot be realized.

Therefore, the twist angle α between the pair of legs 2 and 3 of the staple A is preferably 0° or more and less than 1.9°, and more preferably, 0° or more and less than 1.3°. Further, the twist angle α is desirably 0° or more and less than 0.6°.

With reference to the plane 4 including the centerline 1a of the body portion 1 and the centerline 2a of the leg 2, the twist direction of the pair of legs 2 and 3 of the staple A may be the direction in which the tip 3b of the leg 3 is on the left side of the tip 2b of the leg 2, as shown in FIG. 1, or may be the direction in which the tip 3b of the leg 3 is on the right side of the tip 2b of the leg 2.

It is preferred that the twist angle of the pair of legs 2 and 3 of the staple A be in the above range. However, it is not preferred that there be a large variation in a large number of staples A. In order that no variation is caused, it is preferred that the legs 2 and 3 be twisted by a mechanical method. If variation is caused, it is preferred that the staples are sorted to obtain a group of staples having the twist angle α in the above range.

The processing method for twisting the pair of legs 2 and 3 constituting the staple A as described above is not limited. The staple having a U-shape when viewed from the front side may be manufactured by a known method, and then pressed so that the staple A having the controlled twist angle α can be formed. The pair of legs 2 and 3 may also be fixed by a vice and twisted by rotating the vice.

When the staples A formed as described above are arranged in parallel and loaded in the magazine, good feeding can be realized without tangling the legs.

Figure 2:
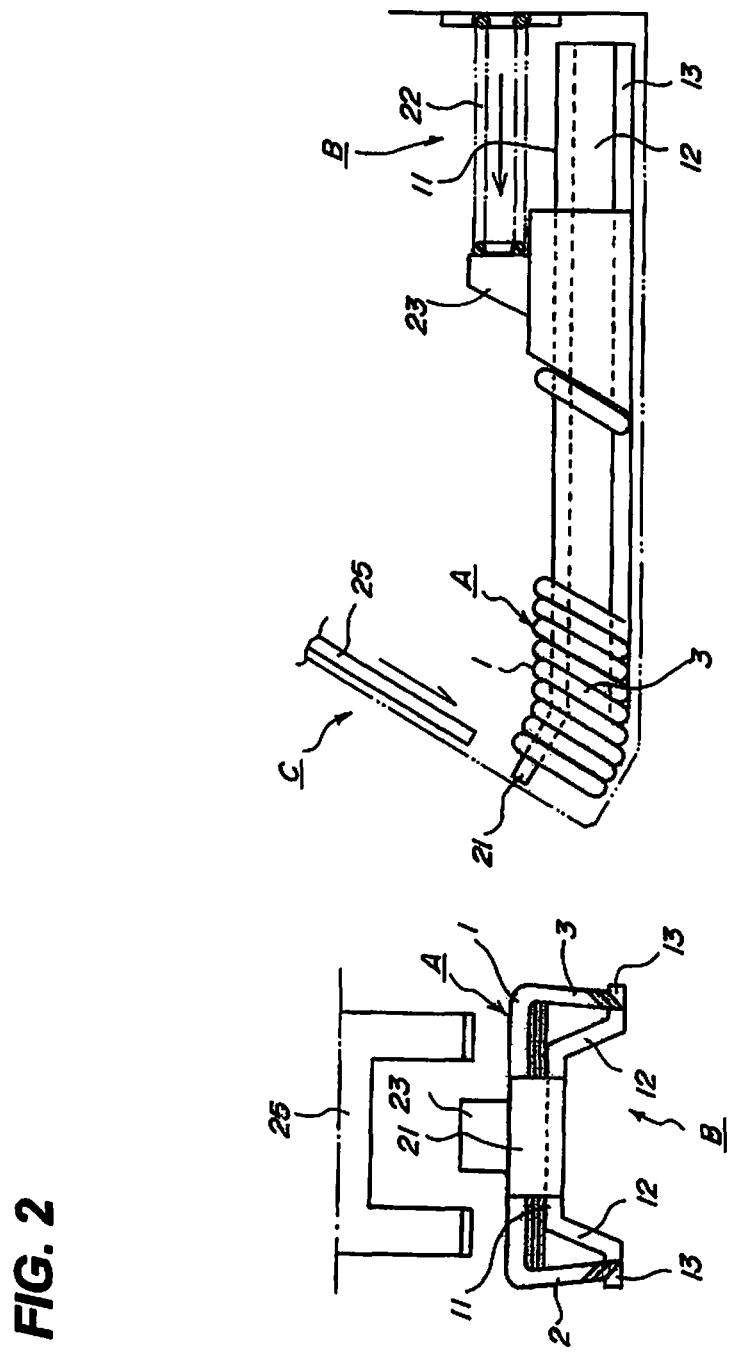
FIG. 2 is a diagram schematically illustrating the configuration of a magazine into which a plurality of staples arranged in parallel is loaded.

The configuration of the magazine will be described with reference to the drawing. FIG. 2 is a diagram schematically illustrating the configuration of the magazine B in which a plurality of staples A arranged in parallel is loaded.

In the figure, the magazine B is constituted by a mold body formed in a Ω shape when viewed from the front side. The magazine B includes a body guiding portion 11 having a planar portion formed at the top thereof, hanging portions 12 hanging from both ends of the body guiding portion 11 in the width direction, and leg guiding portions 13 formed at the lower ends of the hanging portions 12. The magazine B has a length which can satisfy the number of staples A to be loaded which is set corresponding to the specifications of a medical stapler.

The magazine B is formed with the anvil 21 at one end (the left end of FIG. 2), and shapes the staple A located on the anvil 21 to suture an affected part. A pusher 23 urged in the anvil 21 direction by a spring 22 is arranged at the other end (the right end in FIG. 2).

Accordingly, a plurality of staples A loaded in the magazine B is urged in the anvil 21 direction by the pusher 23. When the staple A located on the anvil 21 sutures the affected part and is then discharged, the next staple A moves onto the anvil 21. Thus, the discharge direction in the magazine B is the direction in which the pusher 23 is on the upstream side and the anvil 21 is on the downstream side.

The body guiding portion 11 is in contact with the outer circumferential surfaces of the body portions 1 of the staples A to carry the staples A thereonto, and guides movement in the discharge direction. The body guiding portion 11 also has the function of guiding, not only the staples A, but also the pusher 23 which is in contact with the staples A and is urged in the discharge direction.

For this reason, the body guiding portion 11 has a size substantially equal to or smaller than that of the body portions 1 of the staples A. When the body guiding portion 11 has a size substantially equal to that of the body portions 1 of the staples A, the hanging portions 12 are formed substantially perpendicularly with respect to the body guiding portion 11. When the body guiding portion 11 has a size smaller than that of the body portions 1 of the staples A, as in this embodiment, the hanging portions 12 are formed in a tilted manner.

The hanging portions 12 have a size smaller than the length of the pair of legs 2 and 3 of the staples A. By the configuration of the hanging portions 12, the staples A loaded in the magazine B are tilted. In this way, the hanging portions 12 need not be formed so as to hang perpendicularly from the body guiding portion 11, and may be formed in a tilted manner as in this embodiment. In any case, the hanging portions 12 are required to have a height smaller than the length of the legs 2 and 3.

The leg guiding portions 13 are bent outward from the lower ends of the hanging portions 12 so as to be formed substantially in parallel with the body guiding portion 11, and is in contact with the tips 2b and 3b of the legs 2 and 3 to have a function of guiding movement of the staples A in the discharge direction.

The staples A loaded in the magazine B are placed on the body guiding portion 11 so that the body portions 1 are in contact therewith and are arranged in parallel in a state where the legs 2 and 3 are tilted to the downstream side in the discharge direction (in FIG. 2, the body portions 1 are tilted to the right side and the legs 2 and 3 are tilted to the left side).

According to the above-constituted magazine B, since the loaded staples A are tilted, the medical stapler can be made smaller by reducing its height.

The magazine B is fit into a medical stapler C illustrated by the alternate long and two short dashes line in FIG. 2, and the handle, not shown, is operated. With this operation, a ram 25 is lowered to the anvil 21 side. By the cooperation of the ram 25 and the anvil 21, the U-shaped staples A are shaped into a substantially square shape. According to the shaping process, the tissues of the affected part can be sutured.

When a plurality of staples A of the present invention arranged in parallel is loaded in the magazine B, the legs 2 and 3 of the adjacent staples A are not tangled, whereby smooth feeding can be realized. The staples A can be fit into the medical staplers having different configurations for use.

What is claimed is:

1. A medical staple comprising a straight shaped body portion; and a pair of legs formed at both ends of the body portion, wherein in a state where the medical staple is not used, the legs are tilted at an angle so as to be closer to each other and a centerline of a first one of the legs is entirely twisted at a same angle at a connection point where the first one of the legs is connected to the body portion about a centerline of the body portion with respect to a plane including the centerline of the body portion and a centerline of a second one of the legs.

2. The medical staple as defined in claim 1, wherein the legs are tilted at an angle less than 90 degrees from the body portion so as to have their respective tips being closer to each other than other parts of the leg portions.

3. The medical staple as defined in claim 1, wherein the legs are of a straight shape.

4. A magazine in which a plurality of medical staples each comprising a straight shaped body portion and a pair of legs formed at both ends of the body portion, wherein in a state where the medical staple is not used, the legs are tilted at an angle so as to be closer to each other and a centerline of a first one of the legs is entirely twisted at a same angle at a connection point where the first one of the legs is connected to the body portion about a centerline of the body portion with respect to a plane including the centerline of the body portion and a centerline of a second one of the legs, the staples are arranged in parallel and loaded in a state where the legs are tilted, the magazine comprising a body guiding portion which has a size substantially equal to or smaller than a length of the body portions of the medical staples and carries and guides the body portions of the medical staples thereon; hanging portions which hang from both ends of the body guiding portion and have a size smaller than that of the legs of the medical staples; and leg guiding portions which are formed at lower ends of the hanging portions and guide tips of the legs of the medical staples, wherein the plurality of medical staples is loaded in a state where the legs are tilted to a downstream side in a discharge direction and the body portions are tilted to an upstream side in the discharge direction.

5. The magazine as defined in claim 4, wherein the legs are of a straight shape.

* * * * *